United States Patent [19]
Blankley et al.

[11] Patent Number: 5,525,614
[45] Date of Patent: Jun. 11, 1996

[54] SUBSTITUTED 1,2,3,4-TETRAHYDROISOQUINOLINES WITH ANGIOTENSIN II RECEPTOR ANTAGONIST PROPERTIES

[75] Inventors: Clifton J. Blankley; John C. Hodges; Sylvester Klutchko, all of Ann Arbor, Mich.

[73] Assignee: Warner-Lambert Company, Morris Plains, N.J.

[21] Appl. No.: 509,473

[22] Filed: Jul. 31, 1995

Related U.S. Application Data

[62] Division of Ser. No. 234,759, Apr. 28, 1994, Pat. No. 5,489,686, which is a division of Ser. No. 75,973, Jun. 11, 1993, Pat. No. 5,350,757, which is a division of Ser. No. 885,263, May 19, 1992, Pat. No. 5,246,943.

[51] Int. Cl.[6] .................................................... A61K 31/47
[52] U.S. Cl. ................................................ 514/307; 514/310
[58] Field of Search .......................................... 514/307, 310

[56] References Cited

U.S. PATENT DOCUMENTS

| | | | |
|---|---|---|---|
| 4,812,462 | 3/1989 | Blankley | 514/303 |
| 5,236,934 | 8/1993 | VanAtten | |

FOREIGN PATENT DOCUMENTS

| | | |
|---|---|---|
| 0018104 | 10/1980 | European Pat. Off. |
| 0049605 | 4/1982 | European Pat. Off. |
| 2095252 | 9/1982 | United Kingdom |
| 2116542 | 9/1983 | United Kingdom |

OTHER PUBLICATIONS

M. K. VanAtten, et al., 1,2,3,4-Tetrahydroisoquinoline-3-Carboxylic Acids as Novel, Selective Inhibitors of Angiotensin II Binding to the $AT_2$ site. Aug. 22–27, 1993.
Am. J. Med., 76:4–12 (1984), W. P. Castelli, "Epidemiology of Coronary Heart Disease . . . ".
Hypertension 9:178–187 (1987), G. K. Owens, "Influence of Blood Pressure on Development of Aortic . . . ".
Science 245:186–188 (1989), J. S. Powell et al., "Inhibitors of Angiotensin-Converting . . . ".
Hypertension 18 [Suppl II]:II65–II69 (1991), A. W. Clowes, "Heparin and Cilazapril Together Inhibit . . . ".
Ibid, :II60–II64, W. Osterrieder et al., "Role of Angiotensin II in Injury–Induced Neointima . . . ". 1991.
J. Card. Pharmacol., 16(4):S42–S49 (1990), J. W. Powell, "The Proliferative Response to Vascular Injury . . . ".
Hypertension, 18[Supp. II]:II55–II59 (1991), J. Clozel, "Inhibition of Converting Enzyme and Neointima . . . ".
Ibid, :II47–II54, D. Plissonnier et al., "Effect of Converting Enzyme Inhibition . . . " 1991.
Ibid, :II43–II46, S. Roux, "Cilazapril Inhibits Wall Thickening of Vein Bypass Graft in the Rat". 1991.
Clin. Cardiol., 13:VII–43–48 (1990), A. V. Chobanian, "The Effects of ACE Inhibitors and Other . . . ". 1990.
J. Card. Pharmacol. 15(5):S65–S72, G. Aberg et al., "Effects of Captopril on Atherosclerosis . . . ". 1990.
J. Clin. Invest., 83:1419–1424 (1989), A. Naftilan et al., "Induction of Platelet–derived Growth . . . ".
Biochem. Biophys. Res. Comm., 165(1):196–203 (1989), A. Chiu et al., "Identification of Angiotensin . . . ".
Ibid., 172(3):1195–1202 (1990), A. Chiu et al., "[3H]DUP 753, a highly potent and specific . . . ".
Molecular Pharm., 38:370–377 (1990), D. Dudley et al., "Subclasses of Angiotensin II Binding Sites and . . . ".
Am. J. Pathology, 139(6):1291–1296 (1991), M. Prescott et al "Angiotensin–converting Enzyme Inhibitor . . . ".
Life Sciences, 49:PL–223–PL–228 (1991), R. Kauffman, "Losartan, a Nonpeptide Angiotensin . . . ".
J. Clin. Invest., 88:921–933 (1991) E. Grady et al., "Expression of AT2 Receptors in the Developing . . . ".
Biochem. Biophys. Res. Comm., 179(3):1361–1367 (1991), M. Viswanathan et al., "Changes in Expression . . . ".
Ann. Rev. Physiol., 49:413–435 (1987), M. I. Phillips, "Functions of Angiotensin in the Central . . . ".
Brain Res., 507:341–343 (1990), J. Barnes et al., "Angiotensin II inhibite acetylcholine . . . ".
Pharm. Biochem. & Behavior, 33:573–579 (1989), B. Costall, "The Effects of ACE Inhibitors Captopril . . . ".
Hypertension, 17:425 (1991), Schiavone et al.
Psychosomatic Medicine 35:143–154 (1973), D. Janowsky et al. "Correlations Between Mood, Weight . . . ".
Biochemical Pharmacology, 42(4):715–719 (1991), P. Andrade-Gordon, "Role of Angiotensin . . . ".

Primary Examiner—José G. Dees
Assistant Examiner—Samuel Barts
Attorney, Agent, or Firm—Elizabeth M. Anderson

[57] ABSTRACT

This invention relates to novel substituted 1,2,3,4-tetrahydroisoquinolines which are useful in the treatment of vascular restenosis, various disorders of the central nervous system, in the regulation of female reproductive functions, in cognitive enhancement, in atherosclerosis and in treating excessive AVP secretory disorders. Novel intermediates useful in the preparation of the compounds are also disclosed. Methods of using the compounds and pharmaceutical compositions containing them are disclosed.

1 Claim, No Drawings

SUBSTITUTED 1,2,3,4-TETRAHYDROISOQUINOLINES WITH ANGIOTENSIN II RECEPTOR ANTAGONIST PROPERTIES

This is a Divisional application of U.S. Ser. No. 08/234,759 filed Apr. 28, 1994, now U.S. Pat. No. 5,489,686 which is a Divisional application of U.S. Ser. No. 08/075,973 filed Jun. 11, 1993, now U.S. Pat. No. 5,350,757, which is a Divisional application of U.S. Ser. No. 07/885,263, filed May 19, 1992, now issued U.S. Pat. No. 5,246,943, granted Sep. 21, 1993.

BACKGROUND OF THE INVENTION

U.S. Pat. No. 4,812,462 describes 4,5,6,7-tetrahydro-1H-imidazo[4,5-c]pyridine derivatives as antagonists of angiotensin II (AII) binding at a particular subtype of its cellular receptors, namely the $AT_2$ receptor. By virtue of their $AT_2$ receptor antagonist property, these compounds are disclosed to have utility in the treatment of vascular restenosis, atherosclerosis and disorders related to excessive vasopressin (AVP) secretion, various disorders of the central nervous system (CNS), and also have utility in the regulation of female reproductive functions.

Atherosclerotic arterial occlusive disease is a major cause of morbidity and mortality in the United States (W. P. Castelli, *Am. J. Med.* 76:4–12 (1984)). One important strategy in the treatment of this disorder is the use of various revascularization techniques such as saphenous vein bypass grafting, endarterectomy, and transluminal coronary angioplasty. Unfortunately, the overall success of these revascularization procedures is limited by restenosis due to neointimal hyperplasia. The magnitude of this problem in clinical medicine is increasing with the rising rate of cardiovascular surgery and interventional therapy.

Several factors have been implicated in the pathogenesis of restenosis, including the hormone angiotensin II (Ang II), which is an integral part of the renin-angiotensin system and is a regulator of vascular tone and structure. Ang II is a potent vasoconstrictor which plays a central role in hypertension, congestive heart failure, and vascular diseases. In vivo, Ang II is implicated in the vascular hypertrophy of hypertension since angiotensin converting enzyme (ACE) inhibitors can prevent or attenuate medial hypertrophy in many models of hypertension (G. K. Owens, *Hypertension* 9:178–187 (1987)). Recently it has been found that inhibitors of ACE and angiotensin II antagonists ($AT_1$ subtype) will reduce or attenuate the development of intimal hyperplasia in the rat in response to injury (J. S. Powell, et al, *Science* 245:186–188 (1989); A. W. Clowes, et al, *Hypertension* 18[Suppl II]): II65–II69 (1991), W. Osterrieder, et al, *Hypertension* 18 [Suppl II]: II60–II64 (1991)). These growth inhibitory effects are independent of the hemodynamic effects of ACE inhibitors since treatment with other blood pressure lowering drugs does not inhibit this growth (J. S. Powell, et al, *J. Card. Pharmacol.* 16(Suppl. 4):S42–S49 (1990)). Similar studies have shown that ACE inhibitors prevent vascular growth in response to injury in guinea pigs (J. P. Clozel, et al, *Hypertension* 18 [Suppl II]: II55–II59 (1991) and arterial and venous allograft-induced vascular injury in rats (D. Plissonnier, et al, *Hypertension* 18 [Suppl II]: II47–II54 (1991) and S. P. Roux, et al, *Hypertension* 18 [Suppl II]:-II43–II46 (1991)). Moreover ACE inhibitors can prevent or attenuate atherosclerosis in Watanabe rabbits (A. V. Chobanian, et al, *Clinical Cardiol.* 13:43–48 (1990)) and cholesterol fed primates (G. Abers, et al, *J. Cardiovascular Pharmacol.* 15 (Suppl 5):S56–S72 (1990)).

Angiotensin II has also been shown to play a role in the regulation of vascular smooth muscle cell growth in vitro. In cultured vascular smooth muscle cells, Ang II increases the rates of RNA and protein synthesis and under certain conditions is mitogenic. Moreover, Ang II increases the expression of the proto-oncogenes c-myc, c-jun, and c-fos, as well as growth factors which are involved in Ang II-induced growth, namely, platelet derived growth factor (PDGF), basic fibroblast growth factor, and transforming growth factor-β (TGF-β) (A. J. Naftilan, et al, *J. Clin. Invest.* 83:1419–1424 (1989)).

The results from multiple laboratories suggest the existence of receptor isoforms which possess different binding properties and different intracellular signals. Recently, two classes of receptor antagonists have been used to classify these receptors (A. T. Chiu, et al, *Biochem. Biophys. Res. Comm.* 165:196–203 (1989)). The AT-1 receptors, present on multiple cell types, appear to be coupled via G proteins to phospholipase C. AT-1 receptors are known to be selectively antagonized by Dup753 (A. T. Chiu, et al, *Biochem. Biophys. Res. Comm.* 172:1195–1202 (1990); D. T. Dudley, et al, *Mol. Pharmacol.* 38:370–377 (1990)). Stimulation of this receptor leads to inositol metabolism, increases in intracellular calcium, and activation of protein kinase C. Thus, The AT-1 receptor is the classical membrane Ang II receptor. Blockade of these receptors has been shown to inhibit induced vascular growth. It has been shown that AT-1 receptor antagonists also reduce or attenuate the development of intimal hyperplasia in the rat in response to injury (M. F. Prescott, et al, *American Journal of Pathology* 139:1291–1296 (1991); R. F. Kauffman, et al, *Life Sciences* 49:PL-223–PL-228 (1991), and H. Azuma, et al, *Br. J. Pharmacol.* (1991)).

A second Ang II receptor subtype, AT-2, has been recently discovered and this receptor has a more limited distribution and may not be coupled to G proteins. This receptor has been found to selectively bind compounds utilized in the present invention. The physiologic role of the $AT_2$ receptor has been speculated as mediator of the growth potentiation effects of Ang II. This is based on the observation that this receptor subtype is expressed during fetal development (E. F. Grady, et al, *J. Clin. Invest.* 88:921–933 (1991)). Viswanathan, et al (*Biochem. Biophys. Res. Comm.* 179:1361–1367 (1991)) reported that AT-2 receptors are the predominant isoform in the neonatal vasculature but are only a minor component in that of the adult. The mechanism of action of the compounds utilized in the present invention pertains to their binding to the AT-2 receptors found in proliferating vascular smooth muscle.

The present invention is also related to the discovery that the $AT_2$ receptor is found in the central nervous system (CNS) of mammals, and that compounds of general Formula I described herein are effective in blocking angiotensin II binding at $AT_2$ receptors in various brain regions. Angiotensin II is known to modulate CNS nerve sensitivity to neurotransmitters such as catecholamines, serotonin, and enkephalins, and additionally, angiotensin II is a neurotransmitter that regulates the release of hormones from the brain (Phillips, *Ann. Rev. Physiol.* 49:413–35 (1987)). Agents that block the activity of angiotensin II at $AT_2$ receptors in the CNS will ameliorate disorders associated with abnormal nerve activity and abnormal hormone secretion related to exaggerated $AT_2$ mediated responses to angiotensin II. The compounds of general Formula I, being $AT_2$ antagonists, have possible utility in the treatment and diagnosis of numerous neurological, psychiatric, neuroendocrine, neurodegenerative, and neuroimmunological disorders including, but not limited to, those associated with addiction, anxiety, depression, epilepsy, hyperactivity, memory, pain, Parkinsonism, psychosis, regulation of autonomic functions, sleep, and tardive dyskinesia.

Barnes, et al, in *Brain Research* 507: 341–343 (1990), describe the effects of angiotensin II as an inhibitor of potassium-stimulated release of ACh from human temporal cortex, giving rise to elevated levels of ACh in cortical tissue. Rats treated with an angiotensin converting enzyme (ACE) inhibitor, a drug that blocks the formation of angiotensin II, show reductions in striatal ACh. ACE inhibitors have been shown to enhance cognitive performance in rodent tests of cognition by Costall, et al, in *Pharmacol. Biochem. & Behavior* 33:573–579 (1989).

Since both ACE inhibitors and angiotensin receptor antagonists block the actions of angiotensin II in the brain, it is reasonable that both will enhance cognitive performance.

Another known CNS effect of angiotensin II is stimulation of the release of pituitary and hypothalamic hormones including vasopressin (AVP), oxytocin, adrenocorticotrophic hormone (ACTH), prolactin, and luteinizing hormone (LH). Thus, compounds of general Formula I have utility in treatment of various neuroendocrine disorders that are dependent upon the release of hormones resulting from angiotensin II stimulation of $AT_2$ receptors.

Vasopressin (AVP), also known as antidiuretic hormone, is a peptide hormone which causes decreased urinary output, increased urine density, and reduced thirst. In normal physiology, it is important for conservation of body fluid. Schiavone, et al, in *Hypertension* 17:425 (1991), describe the effects of $AT_2$ antagonists, in antagonizing the angiotensin II-induced secretion of AVP from isolated rat hypothalamo-neurohypophysial explants. Excessive secretion of AVP has been linked to a number of disorders including excessive water retention associated with the female reproductive disorder known as premenstrual syndrome (PMS) (Janowski, et al, *Psychosomatic Medicine* 35:143–154 (1973)) and impaired water excretion with adrenal insufficiency. It has also been linked to Schwartz-Bartter syndrome (an AVP secreting brain tumor), congestive heart failure, liver cirrhosis, nephrotic syndromes, central nervous injuries, acute psychotic states, lung disease, dysmenorrheic uterine hyperactivity, and premature labor (Laszlo, et al, ibid.). Compounds of general Formula I, by virtue of their ability to block angiotensin II-induced AVP secretion, have utility in treatment of the above disorders.

The present invention is also related to the discovery that $AT_2$ receptors are found in female reproductive organs of mammals including uterus (Data in Table 1, hereof and in Dudley, et al, ibid.) and ovaries. The role of angiotensin II in processes leading to ovulation has been reviewed by Andrade-Gordon, et al, in *Biochemical Pharmacology* 42:715–719 (1991). Compounds of general Formula I inhibit the binding of angiotensin II to $AT_2$ receptors in reproductive tissues, including uterus and ovarian follicles and hence antagonize the effects of angiotensin II therein.

$AT_2$ receptor antagonists thus have potential utilities in the regulation of fertility and the menstrual cycle.

SUMMARY OF THE INVENTION

The present invention relates to novel substituted 1,2,3,4-tetrahydroisoquinoline derivatives of Formula I

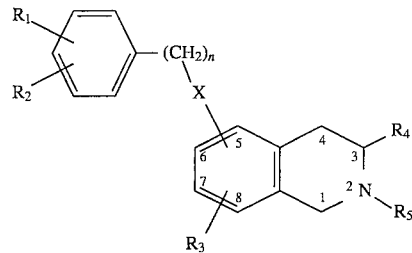

or a pharmaceutically acceptable salt thereof wherein $R_1$, $R_2$, n, X, $R_3$, $R_4$, and $R_5$ are as defined below.

These compounds have potent and selective $AT_2$ antagonist activity (with no $AT_1$ antagonist properties). By virtue of this activity, compounds of Formula I have utilities including treatment of vascular smooth muscle proliferative diseases such as postsurgical vascular restenosis and atherosclerosis; treatment of various disorders of the CNS including disorders of memory and disorders related to excessive AVP secretion such as Schwartz-Bartter syndrome and PMS; and regulation of female reproductive functions.

The invention also includes a pharmaceutical composition comprising an antiatherosclerotic effective amount of a compound of Formula I above in admixture with a pharmaceutically acceptable carrier or excipient and a method for treatment in a mammal suffering therefrom which comprises administering to said mammal the above pharmaceutical composition in unit dosage form.

Further, the invention includes a pharmaceutical composition comprising an amount of a compound of Formula I above effective for treating female reproductive disorders in admixture with a pharmaceutically acceptable carrier or excipient, and a method for treating the same in a mammal suffering therefrom comprising administering to said patient the above pharmaceutical composition in unit dosage form.

The invention also includes a pharmaceutical composition comprising an amount effective for treating restenosis of a compound of Formula I above in admixture with a pharmaceutically acceptable carrier or excipient and a method of treating restenosis in a mammal suffering therefrom comprising administering to said mammal the above pharmaceutical composition in unit dosage form.

Also, the invention includes a pharmaceutical composition comprising an amount of a compound of Formula I above effective for treating cognitive decline in admixture with a pharmaceutically acceptable carrier or excipient; and a method of treating cognitive decline in a mammal suffering therefrom comprising administering to said mammal the above pharmaceutical composition in unit dosage form.

The invention includes a pharmaceutical composition comprising an amount of a compound of Formula I above, effective to treat disorders related to excessive AVP secretion in admixture with a pharmaceutically acceptable carrier or excipient, and a method for treating such disorders in a patient suffering therefrom comprising administering to said patient the above pharmaceutical composition in unit dosage form.

The invention includes a pharmaceutical composition comprising an amount of a compound of Formula I above, effective to treat vascular cardiac hypertrophy in admixture with a pharmaceutically acceptable carrier or excipient, and a method for treating such disorders in a patient suffering therefrom comprising administering to said patient the above pharmaceutical composition in unit dosage form.

The instant invention further includes methods for making compounds of Formula I and novel intermediates useful in the preparation.

DETAILED DESCRIPTION

The instant invention is for compounds of formula

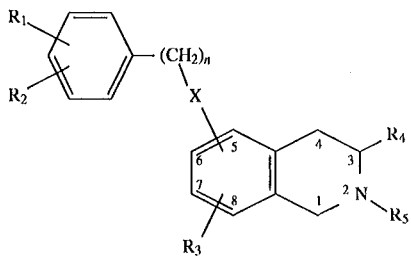

or a pharmaceutically acceptable salt thereof wherein:

$R_1$ and $R_2$ are each independently hydrogen, lower alkyl, halogen, hydroxy, alkoxy, amino, alkylamino, dialkylamino, acylamino, $CF_3$, carboxy, carboalkoxy, hydroxyalkyl, aminoalkyl, and nitro;

n is an integer from zero to 4;

X is absent, O, S, NH, N-alkyl, and is attached to the tetrahydroisoquinoline at the 5 or 6 position;

$R_3$ is hydrogen, alkoxy, aryloxy, alkylthio, or halogen attached either at the 6, 7, or 8 position;

$R_4$ is hydrogen, alkyl, hydroxyalkyl, $CO_2R_6$, $CON(R_6)_2$ wherein $R_6$ is hydrogen or lower alkyl; and $R_5$ is alkyl, aryl, aralkyl which can be unsubstituted or substituted on the alkyl and/or on the aryl portion, diaralkyl (the aryl portion can be unsubstituted or substituted), $COR_7$, $SO_2R_7$ wherein $R_7$ is aralkyl, alkyl, diaralkyl, $OR_8$, $NR_8R_9$ wherein $R_8$ and $R_9$ are each independently hydrogen, alkyl, cycloalkyl, aryl, or aralkyl. More preferred compounds of the invention are those of Formula I wherein $R_1$ and $R_2$ are each independently hydrogen, lower alkyl, alkoxy, amino, carboxy, and nitro;

n is an integer of from 0 to 3;

X is O, S, or NH substituted at the 5 position;

$R_3$ is hydrogen, alkoxy, or halogen substituted at the 6 position;

$R_4$ is hydrogen, alkyl, hydroxyalkyl, $CO_2R_6$, $CON(R_6)_2$; and $R_5$ is alkyl, aryl, or $COR_7$.

Still more preferred compounds of the invention are those of Formula I wherein $R_1$ and $R_2$ are each independently hydrogen, lower alkyl, alkoxy, carboxy, and nitro;

n is an integer of from 0 to 2;

X is O substituted at the 5 position;

$R_3$ is alkoxy substituted at the 6 position;

$R_4$ is $CO_2R_6$, or $CON(R_6)_2$; and $R_5$ is $COR_7$ wherein $R_7$ is diaralkyl or $NR_8R_9$ wherein $R_8$ and $R_9$ are each independently hydrogen, alkyl, or aryl and the aryl group may be substituted.

Yet still more preferred compounds of the invention are those of Formula I wherein $R_1$ and $R_2$ are each independently hydrogen, methoxy, carboxy, methyl, nitro, or amino;

n is 0, 1, or 2;

X is O, NH;

$R_3$ is H, or $OCH_3$;

$R_4$ is $COOH$, $COOCH_3$, $COOC_2H_5$, $CONH_2$, and

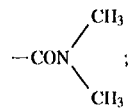

and $R_5$ is hydrogen,

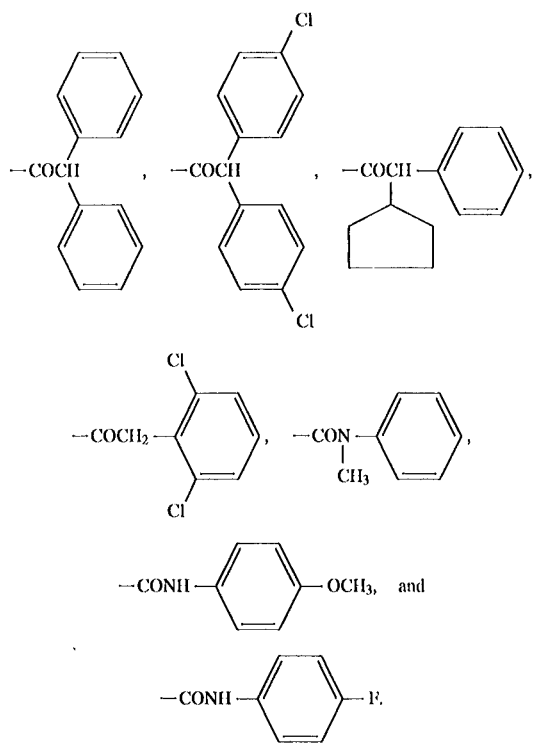

Certain compounds of the present invention possess one or more chiral centers and each center may exist in the R or S configuration. The present invention includes all enantiomeric and diastereomeric forms as well as the appropriate mixtures thereof.

Still more preferred compounds are:

2-(Diphenylacetyl)-6-ethoxy-1,2,3,4-tetrahydro-5-(phenylmethoxy)-3-isoquinolinecarboxylic acid, 2-(Diphenylacetyl)-1,2,3,4-tetrahydro-6-methoxy-5-(phenylmethoxy)-3-isoquinolinecarboxylic acid, 2-(2,2-Diphenylethyl)-1,2,3,4-tetrahydro-6-methoxy-5-(phenylmethoxy)-3-isoquinolinecarboxylic acid, 2-Butyl-1,2,3,4-tetrahydro-6-methoxy-5-(phenylmethoxy)-3-isoquinolinecarboxylic acid, 2-(Diphenylacetyl)-1,2,3,4-tetrahydro-6-methoxy-5-(phenylmethoxy)-3-isoquinolinecarboxylic acid, 2-[(Diphenylmethyl)sulfonyl]-1,2,3,4-tetrahydro-6-methoxy-5-(phenylmethoxy)-3-isoquinolinecarboxylic acid, and 1,2,3,4-Tetrahydro-6-methoxy-2-phenyl-5-(phenylmethoxy)-3-isoquinolinecarboxylic acid.

Yet still more preferred compounds are:

5-[(4-Aminophenyl)methoxy]-2-(diphenylacetyl)-1,2,3,4-tetrahydro-6-methoxy-3-isoquinolinecarboxylic acid, 5-[(4-Amino-3-methylphenyl)methoxy]-2-(diphenylacetyl)-1,2,3,4-tetrahydro-6-methoxy-3-isoquinolinecarboxylic acid, 5-[[4-(Dimethylamino)-3-methylphenyl]methoxy]-2-(diphenylacetyl)-1,2,3,4-tetrahydro-6-methoxy-3-isoquinolinecarboxylic acid,
(S)-2-(Diphenylacetyl)-1,2,3,4-tetrahydro-6-methoxy-5-(phenylmethoxy)-3-isoquinolinecarboxylic acid,
(R)-2-(Diphenylacetyl)-1,2,3,4-tetrahydro-6-methoxy-5-(phenylmethoxy)-3-isoquinolinecarboxylic acid,
2-(Diphenylacetyl)-1,2,3,4-tetrahydro-6-methoxy-5-[(phenylmethyl)thio]-3-isoquinolinecarboxylic acid,
2-(Diphenylacetyl)-1,2,3,4-tetrahydro-6-(methylthio)-5-(phenylmethoxy)-3-isoquinolinecarboxylic acid,
2-(Diphenylacetyl)-1,2,3,4-tetrahydro-6-methoxy-5-[(phenylmethyl)amino]-3-isoquinolinecarboxylic acid,
2-(Diphenylacetyl)-1,2,3,4-tetrahydro-6-methoxy-5-[methyl (phenylmethyl)amino]-3-isoquinolinecarboxylic acid,
2-(Diphenylacetyl)-1,2,3,4-tetrahydro-6-methoxy-5-(phenylthio)-3-isoquinolinecarboxylic acid,
2-(Diphenylacetyl)-1,2,3,4-tetrahydro-6-methoxy-5-(phenylthio)-3-isoquinolinecarboxylic acid,
2-(Diphenylacetyl)-1,2,3,4-tetrahydro-6-methoxy-5-[methyl(phenylamino)]-3-isoquinolinecarboxylic acid,
2-(Diphenylacetyl)-1,2,3,4-tetrahydro-6-methoxy-5-(phenylmethyl)-3-isoquinolinecarboxylic acid,
2-(Diphenylacetyl)-1,2,3,4-tetrahydro-6-methoxy-5-(2-phenylethyl)-3-isoquinolinecarboxylic acid,
2-(Diphenylacetyl)-1,2,3,4-tetrahydro-6-methoxy-5-phenyl-3-isoquinolinecarboxylic acid,
2-(Diphenylacetyl)-1,2,3,4-tetrahydro-5-(phenylmethoxy)-3-isoquinolinecarboxylic acid,
2-(Diphenylacetyl)-1,2,3,4-tetrahydro-6-methoxy-5-(phenylmethoxy)-3-isoquinolinecarboxamide, and
2-(Diphenylacetyl)-1,2,3,4-tetrahydro-N,N-dimethyl-6-methoxy-5-(phenylmethoxy)-3-isoquinolinecarboxamide.

The most preferred compounds of the invention are:
2-(Diphenylacetyl)-1,2,3,4-tetrahydro-6-methoxy-5-(phenylmethoxy)-3-isoquinolinecarboxylic acid,
2-(Diphenylacetyl)-1,2,3,4-tetrahydro-7-methoxy-6-(phenylmethoxy)-3-isoquinolinecarboxylic acid,
2-(Diphenylacetyl)-1,2,3,4-tetrahydro-6-methoxy-5-(2-phenylethoxy)-3-isoquinolinecarboxylic acid,
2-[Bis(4-chlorophenyl)acetyl]-1,2,3,4-tetrahydro-6-methoxy-5-(phenylmethoxy)-3-isoquinolinecarboxylic acid,
2-(Cyclopentylphenylacetyl)-1,2,3,4-tetrahydro-6-methoxy-5-(phenylmethoxy)-3-isoquinolinecarboxylic acid,
2-[(2,6-Dichlorophenyl)acetyl]-1,2,3,4-tetrahydro-6-methoxy-5-(phenylmethoxy)-3-isoquinolinecarboxylic acid,
1,2,3,4-Tetrahydro-6-methoxy-2-[(methylphenylamino)carbonyl]-5-(phenylmethoxy)-3-isoquinolinecarboxylic acid,
1,2,3,4-Tetrahydro-6-methoxy-2-[[(4-methoxyphenyl)amino]carbonyl]-5-(phenylmethoxy)-3-isoquinolinecarboxylic acid,
2-[[(4-Fluorophenyl)amino]carbonyl]-1,2,3,4-tetrahydro-6-methoxy-5-(phenylmethoxy)-3-isoquinolinecarboxylic acid,
2-(Diphenylacetyl)-1,2,3,4-tetrahydro-6-methoxy-5-phenylmethoxy-3-isoquinolinecarboxylic acid, ethyl ester,
5-[(4-Carbomethoxyphenyl)methoxy]-2-(diphenylacetyl)-1,2,3,4-tetrahydro-6-methoxy-3-isoquinolinecarboxylic acid, ethyl ester,
5-(4-Carboxyphenylmethoxy)-2-(diphenylacetyl)-1,2,3,4-tetrahydro-6-methoxy-3-isoquinolinecarboxylic acid,
2-(Diphenylacetyl)-1,2,3,4-tetrahydro-6-methoxy-5-[(4-methoxy-3-methylphenyl)methoxy]-3-isoquinolinecarboxylic acid, ethyl ester,
2-(Diphenylacetyl)-1,2,3,4-tetrahydro-6-methoxy-5-[(4-methoxy-3-methylphenyl)methoxy]-3-isoquinolinecarboxylic acid,
2-(Diphenylacetyl)-1,2,3,4-tetrahydro-6-methoxy-5-(4-nitrophenoxy)-3-isoquinolinecarboxylic acid, methyl ester,
5-(4-Aminophenoxy)-2-(diphenylacetyl)-1,2,3,4-tetrahydro-6-methoxy-3-isoquinolinecarboxylic acid, methyl ester,
5-(4-Aminophenoxy)-2-(diphenylacetyl)-1,2,3,4-tetrahydro-6-methoxy-3-isoquinolinecarboxylic acid, and,
(+)-2-(Diphenylacetyl)-1,2,3,4-tetrahydro-6-methoxy-5-(phenylmethoxy)-3-isoquinolinecarboxylic acid.

Novel intermediates of the invention include:
3-Methoxy-2-(phenylmethoxy)phenylalanine,
4-Methoxy-3-(phenylmethoxy)phenylalanine,
3-Methoxy-2-(2-phenylethoxy)phenylalanine,
3-Methoxy-2-(4-nitrophenoxy)phenylalanine,
1,2,3,4-Tetrahydro-6-methoxy-5-(phenylmethoxy-3-isoquinolinecarboxylic acid,
1,2,3,4-Tetrahydro-7-methoxy-6-(phenylmethoxy)-3-isoquinolinecarboxylic acid,
1,2,3,4-Tetrahydro-6-methoxy-5-(2-phenylethoxy)-3-isoquinolinecarboxylic acid,
1,2,3,4-Tetrahydro-6-methoxy-5-(4-nitrophenoxy)-3-isoquinolinecarboxylic acid,
1,2,3,4-Tetrahydro-5-hydroxy-6-methoxy-3-isoquinolinecarboxylic acid,
1,2,3,4-Tetrahydro-6-methoxy-5-(phenylmethoxy)-3-isoquinolinecarboxylic acid, ethyl ester,
1,2,3,4-Tetrahydro-5-hydroxy-6-methoxy-3-isoquinolinecarboxylic acid, ethyl ester,
1,2,3,4-Tetrahydro-6-methoxy-5-(4-nitrophenoxy)-3-isoquinolinecarboxylic acid, methyl ester,
N-Acetyl-3-methoxy-2-(phenylmethoxy)phenylalanine,
1,2,3,4-Tetrahydro-5-hydroxy-6-methoxy-2-[methyl(phenylamino)carbonyl]-3-isoquinolinecarboxylic acid, and
2-(Diphenylacetyl)-1,2,3,4-tetrahydro-5-hydroxy-6-methoxy-3-isoquinolinecarboxylic acid, ethyl ester.

Certain compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I are capable of further forming both pharmaceutically acceptable acid addition and/or base salts. All of these forms are within the scope of the present invention.

Pharmaceutically acceptable acid addition salts of the compound of Formula I include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate(see, for example, Berge, S. M., et al, "Pharmaceutical Salts," *Journal of Pharmaceutical Science* 66:1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali or alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge, S. M., et al, "Pharmaceutical Salts," ibid.

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

In the compounds of Formula I, the term "alkyl" means a straight or branched hydrocarbon radical having from one to eight carbon atoms and includes, for example, methyl, ethyl, n-propyl, isopropyl, n-butyl, sec-butyl, isobutyl, tert-butyl, n-pentyl, n-hexyl, and the like except where specifically stated otherwise.

The term halogen includes fluorine, chlorine, bromine, and iodine; the more preferred halogens are fluorine and chlorine.

The term alkoxy refers to an alkyl radical attached to the remainder of the molecule by oxygen; this includes but is not limited to methoxy, ethoxy, and propoxy groups.

The terms alkylamino and dialkylamino refer to one or two alkyl radicals attached to a nitrogen atom; N-methylamino and N,N-dimethylamino are examples.

Acylamino includes such groups as $CH_3CONH$, $CH_3CH_2CONH$, $PhCONH$.

Carboalkoxy refers to groups such as alkyl esters of carboxylic acids.

Hydroxyalkyl refers to alkyl groups of from one to six carbon atoms which may be straight or branched, such as $CH_2OH$.

Aryl is an aromatic hydrocarbon such as phenyl, naphthyl, and the like. The aryl may be unsubstituted or substituted by one or more selected from alkyl such as methyl or ethyl, alkoxy such as methoxy or ethoxy, hydroxy, halogen such as fluorine, chlorine, and bromine, $NO_2$, $NH_2$, NHalkyl, $N(alkyl)_2$, $SCH_3$, and SH.

Aralkyl and diaralkyl are as defined above for alkyl and for aryl. Such groups include but are not limited to $PhCH_2$— and $Ph_2CH$—. The groups can be unsubstituted or substituted on the alkyl and/or on the aryl portion such as the group

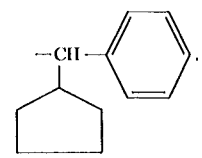

Substituents on the alkyl portion are, for example, alkyl, dialkyl, or cycloalkyl.

Cycloalkyl is a cyclic group of from three to six carbon atoms, preferred cycloalkyls are cyclopentyl and cyclohexyl.

The strategy for preparation of compounds of Formula I is exemplified in Scheme I. It involves benzylations of a phenolic aldehyde such as 1 with a benzyl halide

SCHEME I

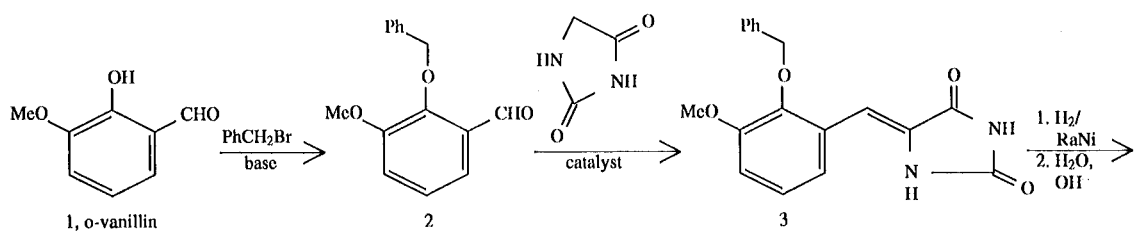

-continued
SCHEME I

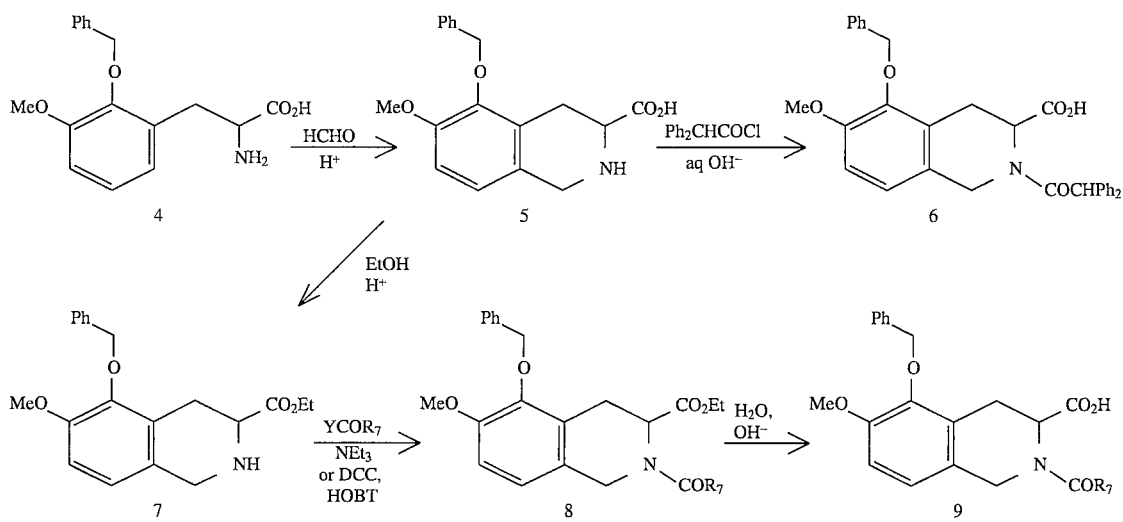

Y = OH, Cl, active ester in the presence of a weak inorganic base such as $Na_2CO_3$, $K_2CO_3$, or $CsCO_3$ and the like in a polar solvent such as ethanol, methanol, DMF, or DMA and the like. Preferred conditions for the alkylation employ one to five equivalents of powdered potassium carbonate in ethanol at 25° to 80° C. for 1 to 12 hours. The benzyloxybenzaldehyde derivative 2 is condensed with hydantoin. The condensation is performed under weakly acidic conditions in a solvent such as acetic acid or propanoic acid and the like using an appropriate catalyst such as β-alanine or sodium acetate at temperatures of 25° to 135° C. Preferred conditions for the condensation with aldehyde 2 employ 1 to 1.2 equivalents of hydantoin and 0.1 to 0.3 equivalents of β-alanine in glacial acetic acid at reflux for 1 to 12 hours. Reduction conditions for the benzylidene hydantoin 3 are designed to prevent debenzylation of the benzyl ether; thus either a zinc-hydrochloric acid method or hydrogenation with Raney nickel catalyst is preferred.

In the zinc-acid method 2 to 4 equivalents of zinc powder is added to a stirred suspension of the benzylidene hydantoin in a polar solvent such as methanol containing 10 to 100 equivalents of concentrated hydrochloric acid at 50° to 100° C. for 0.5 to 2 hours. The Raney nickel catalytic hydrogenation of the benzylidene hydantoin is effected by dissolution of the hydantoin in a polar solvent such as methanol containing a strong base, such as, but not limited to, 1.1 equivalents of KOH or $(Me)_4NOH$. The preferred base for solubility purposes is $(Me)_4NOH$. Other catalysts such as 20% palladium/carbon are effective with this basic solvent system when debenzylation is not a problem (see reduction of the phenylethoxy benzylidene hydantoin in Example 8).

The intermediate substituted phenylalanine derivatives (4) are generated from the above prepared benzyl hydantoins by a strong base hydrolysis utilizing 5% to 50% NaOH, KOH, or LiOH in aqueous medium at temperatures of 50° to 120° C. for 1 to 48 hours.

The cyclization of the phenylalanine 4 to a tetrahydroisoquinoline 5 proceeds under acidic conditions. Suitable conditions include 1 to 10 equivalents of 1 to 3N hydrochloric or sulfuric acid in the presence of 1 to 10 equivalents of formaldehyde, either as an aqueous solution or in the form of its dimethyl acetal, methylal, at 25° to 100° C. The preferred acid is 1N hydrochloric acid with methylal as the formaldehyde source.

The target acylated tetrahydroisoquinoline 6 may be obtained by a Schotten-Baumann type of acylation of the amino acid 5 with an acid chloride. The preferred conditions involve adding an acid chloride acylating agent (0.12 mole, 20% excess) either neat or as a solution in methylene chloride, ethyl acetate, THF, or dioxane, to a cooled (0° to 5° C.) vigorously stirred mixture of the amino acid, 0.20 to 0.22 mole of a strong base such as NaOH, KOH, or $(Me)_4NOH$, and water with any of the above solvents. Adjustment of the pH to 3 yields the acylated amino acid 6. The preferred base is $(Me)_4NOH$ and the solvent is methylene chloride.

Alternatively, compound 5 may be esterified first with anhydrous alcohols and hydrogen chloride to 7 which are then acylated with $YCOR_7$ where Y is OH or an activating moiety such as halogen or an active ester group. Subsequent base hydrolysis of the esters 8 with alcoholic solvents such as methanol or ethanol and 1 to 2N sodium hydroxide at 50° to 80° C. for 0.25 to 6 hours gives the carboxylic acid derivatives such as 9.

An alternate method of preparing various phenol ethers is described in Scheme II.

SCHEME II

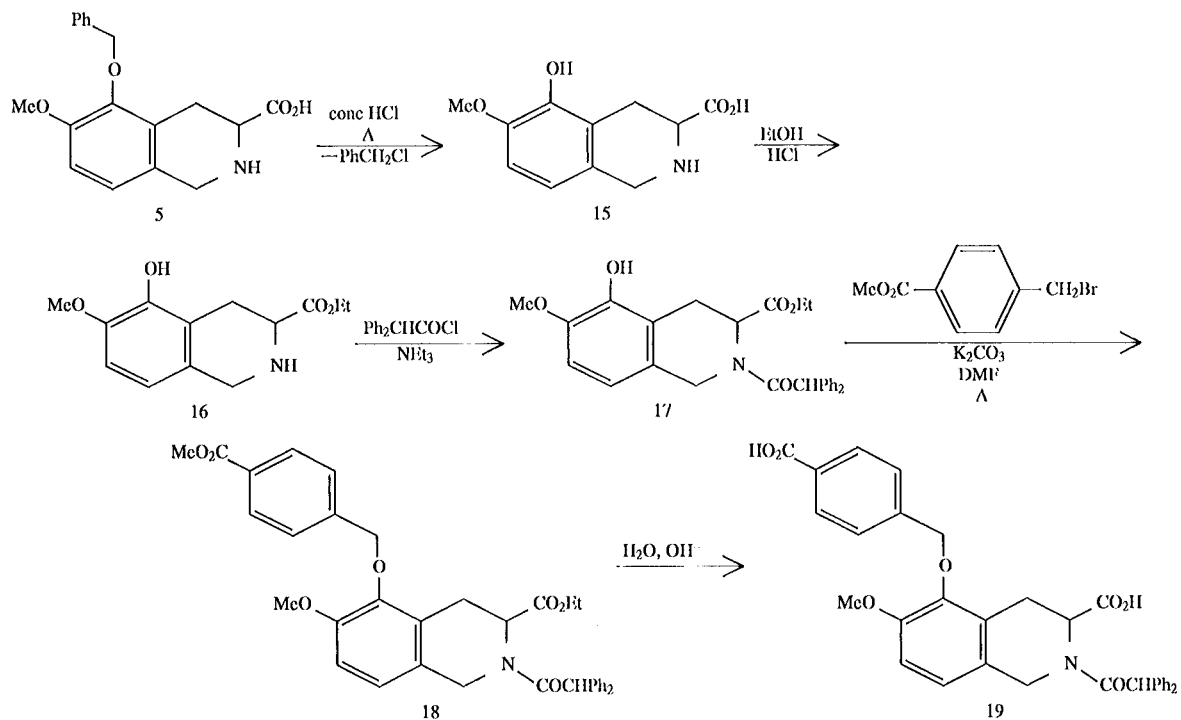

A phenol intermediate 15 is generated by debenzylation of 5 either by catalytic hydrogenolysis with 20% palladium/carbon or by warming 5 to 50° to 100° C. with concentrated hydrochloric acid. The preferred method is concentrated hydrochloric acid at reflux for 10 minutes. The esterification to 16 is accomplished by the standard Fisher method with absolute ethanol-hydrogen chloride.

Acylation of 16 with an acid chloride under anhydrous conditions in an aprotic solvent such as methylene chloride, THF, or ether with an organic amine, such as triethylamine as a proton acceptor yields compounds like 17 which can now be alkylated to compounds like 18 by a variety of alkylating agents. Conditions for the alkylation are similar to those described for compound 1 in Scheme I. The conditions in this case are DMF as a solvent, $NA_2CO_3$ as a base, and temperature at reflux for a 5-minute reaction time. Base hydrolysis of 18 with 2N sodium hydroxide in methanol at reflux yields the product 19.

Scheme III describes an alternate method of preparing intermediate substituted phenylalanine derivatives (4, 14).

SCHEME III

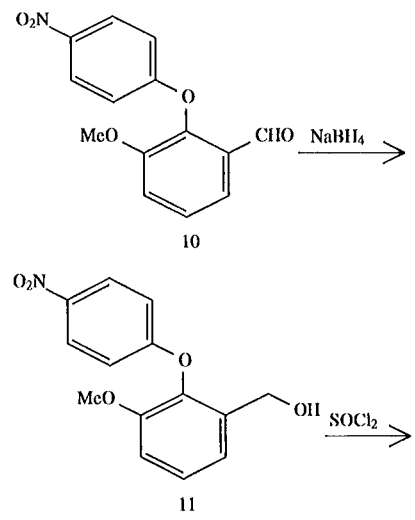

-continued
SCHEME III

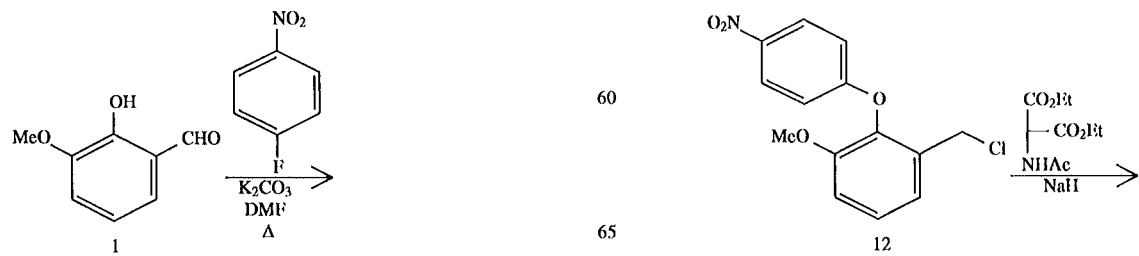

-continued
SCHEME III

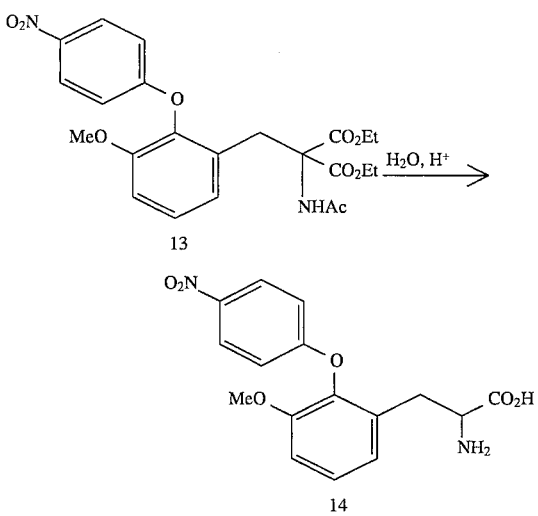

The example in Scheme III describes a sequence starting from a p-nitrophenoxy benzaldehyde 10. Compound 10 is prepared by acylation of I with p-fluoronitrobenzene in DMF at reflux for 10 minutes with powdered $K_2CO_3$ as a proton acceptor. The remainder of the sequence involves standard methods of preparing phenylalanine derivatives (4, 14) through the acetamidomalonate method. A typical compound active in a rabbit uterus binding assay for detecting angiotensin type 2 ($AT_2$) antagonists is compound 6 below. $AT_2$ Binding Assay is a modification of the procedure by D. T. Dudley, et al, *Mol. Pharmacol.* 38:370 (1990). The binding affinity of Compound 6 is $IC_{50}$ 2.8 nM.

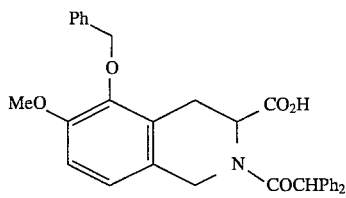

Other compounds of this invention and binding activities are listed in the Table I below.

TABLE I

| Example | $AT_2$ Binding $IC_{50}$ (nM) |
|---|---|
| 26 | 8.4 |
| 20 (Compound 6) | 2.8 |
| 23 | 24.2 |
| 25 | 117.0 |
| 24 | 1.6 |
| 22 | 8.9 |
| 21 | 58.5 |
| 27 | 1,110.0 |
| 35 | 1.9 |
| 30 | 151.0 |
| 33 | 752.0 |

As can be seen in Table I above, Example 20 (Compound 6) has a high binding affinity for the $AT_2$ receptor site. Since it was inactive in the $AT_1$ binding assay at $10^{-5}$M concentration, it is highly selective for the $AT_2$ site.

Based on the above data, the compounds of the instant invention are expected to have utility in treating restenosis, atherosclerosis and disorders involving excessive AVP secretion, CNS disorders, certain female reproductive disorders, and certain cognitive disorders.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents. It can also be encapsulating material. In powders, the carrier is a finely divided solid which is in admixture with the finely divided active compound. In the tablet the active compound is mixed with a carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The confounds of the present invention may be administered orally, buccally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques such as infusion pump.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquified form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gum, resins, methylcellulose, sodium carboxymethyl-cellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerin, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 1000 mg, preferably 5 to 200 mg according to the particular application and the potency of the active ingredient. The compositions can, if desired, also contain other compatible therapeutic agents.

In therapeutic use the mammalian dosage range for a 70 kg subject is from 0.1 to 1500 mg/kg of body weight per day or preferably 1 to 500 mg/kg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are illustrative of the instant invention; they are not intended to limit its scope in any way.

EXAMPLE 1

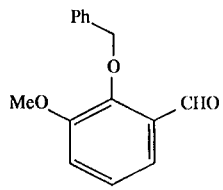

3-Methoxy -2-(phenylmethoxy)benzaldehyde

A mixture of 196.0 g (1.30 mole) of o-vanillin (Aldrich), 200 g of benzyl bromide (Aldrich), 500 g of anhydrous potassium carbonate and 1,500 mL of absolute ethanol is heated, with stirring, at reflux for 6 hours. After cooling, the supernatant is decanted and the remainder is filtered. The combined filtrate and supernatant is concentrated at reduced pressure to remove solvent. The remaining oil is extracted into 1 L of ether. The ether solution is washed with 500 mL of water, 600 mL of 1% potassium hydroxide solution, and 500 mL of water and then dried (potassium carbonate) and concentrated to give 263.4 g (84% yield) of product; mp 41°–43° C. Reported mp, 43° C. (Chem. Abstr. 62:16110a).

EXAMPLE 2

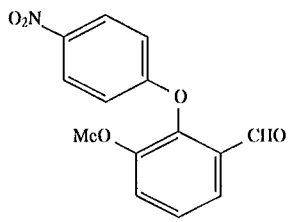

3-Methoxy-2-(4-nitrophenoxy)benzaldehyde

A mixture of 14.10 g (0.10 mole) of 4-fluoronitrobenzene, 16.40 g (0.10 mole) of o-vanillin, 30 g of powdered potassium carbonate, and 40 mL of DMF is heated with stirring to the boiling point. After 10 minutes the mixture is cooled to 100° C. and 300 mL of ice water is added. Petroleum ether (200 mL) is added and the entire mixture is filtered and the cake is washed with 200 mL of water and then 200 mL of petroleum ether. The damp cake is slurried in 100 mL of methanol and filtered; wt 19.50 g (71% yield); mp 130°–131° C.; mass spectrum (DEI), 273 (M$^+$).

EXAMPLE 3

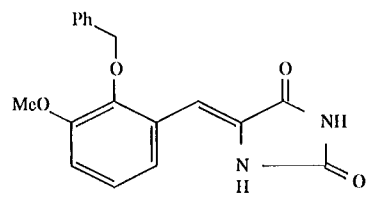

5-[[3-Methoxy-2-(phenylmethoxy)phenyl]methylene]-2,4-imidazolidinedione

A solution of 96.90 g (0.40 mole) of 2-benzyloxy-3-methoxybenzaldehyde, 48.04 g (0.48 mole) of hydantoin, 8.02 g (0.09 mole) of β-alanine, and 200 mL of glacial acetic acid is stirred at reflux for 6 hours. Water (500 mL) is added and the separated solid is filtered, washed well with water, methanol, and then ether; wt 109.00 g (84% yield); mp 210°–212° C.

Anal. Calc. for $C_{18}H_{16}N_2O_4$: C, 66.65; H, 4.97; N, 8.64. Found: C, 66.77; H, 4.84; N, 8.74.

EXAMPLE 4

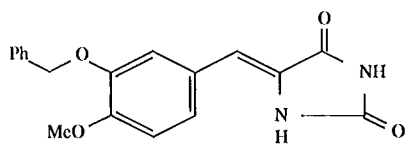

5-[[4-Methoxy-3-(phenylmethoxy)phenyl]methylene]-2,4-imidazolidinedione

This compound is prepared from 3-benzyloxy-4-methoxybenzaldehyde (Aldrich) and hydantoin by the procedure described in Example 3; mp 242°–244° C.

Anal. Calc. for $C_{18}H_{16}N_2O_4$: C, 66.65; H, 4.97; N, 8.64. Found: C, 67.01; H, 5.07; N, 8.64.

EXAMPLE 5

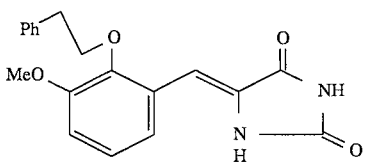

5-[[3-Methoxy-2-(2-phenylethoxy)phenyl]methylene]-2,4-imidazolidinedione

This compound is prepared from 2-(2-phenylethoxy)-3-methoxybenzaldehyde of Example 46 by the procedure of Example 3; mp 199°–201° C.

Anal. Calc. for $C_{19}H_{18}N_2O_4$: C, 67.44; H, 5.36; N, 8.28. Found: C, 67.48; H, 5.53; N, 8.36.

EXAMPLE 6

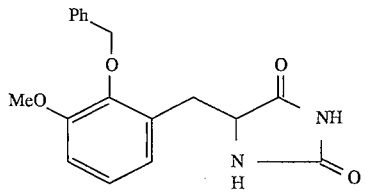

(RS)-5-[[3-Methoxy-2-(phenylmethoxy)phenyl]methyl]-2,4-imidazolidinedione

Zinc powder (40.00 g; 0.61 mole) is added to a stirred suspension of 48.00 g (0.16 mole) of the benzylidine hydantoin from Example 3 in 1,200 mL of methanol under nitrogen. Concentrated hydrochloric acid (30 mL) is added and the mixture is heated on the steam bath for 20 minutes (after 10 minutes the starting benzylidene hydantoin dissolves). Another 30 mL of concentrated hydrochloric acid is added and the mixture is heated at reflux for another 20 minutes. The cooled (50° C.) mixture is cautiously filtered and the cake washed with 100 mL of methanol. Water (500 mL) is added to the filtrate to yield 24.60 g of crystalline product; mp 202°–204° C.

Recrystallization from methanol gives pure product; mp 205°–207° C. Anal. Calc. for $C_{18}H_{18}N_2O_4$: C, 66.24; H, 5.56; N, 8.59. Found: C, 66.10; H, 5.68; N, 8.60.

EXAMPLE 7

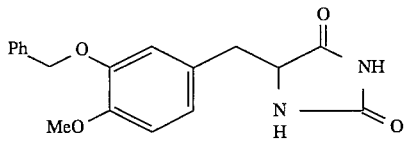

(RS)-5-[[4-Methoxy-3-(phenylmethoxy)phenyl]methyl]-2,4-imidazolidinedione

A solution of 16.20 g (0.05 mole) of the benzylidene hydantoin from Example 4 in 100 mL of methanol and 25.0 g (0,055 mole) of 20% tetramethylammonium hydroxide-in-methanol is reduced with hydrogen and Raney nickel catalyst. After the theoretical uptake of hydrogen the mixture is filtered and acetic acid (ca 5 mL) and then water is added until just turbid. The first crop of solid is filtered. This is starting material. An additional 2 L of water is added to precipitate the product as crop 2; wt 7.60 g (47% yield). Recrystallization from methanol gives pure product; mp 155°–157° C.

Anal. Calc. for $C_{18}H_{18}N_2O_4$: C, 66.24; H, 5.56; N, 8.59. Found: C, 66.19; H, 5.60; N, 8.68.

EXAMPLE 8

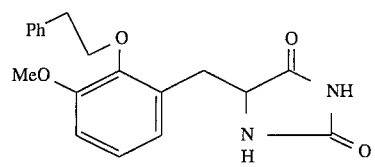

(RS)-5-[[3-Methoxy-2-phenylethoxy)phenyl]methyl]-2,4-imidazolidinedione

A solution of 16.92 g (0.05 mole) of the benzylidene hydantoin from Example 5 in 100 mL of methanol and 25.0 g (0,055 mole) of 20% tetramethylammonium hydroxide-in-methanol is reduced with hydrogen and 20% palladium on carbon catalyst. After the theoretical amount of hydrogen is absorbed, the catalyst is filtered. Acetic acid (ca 5 mL) and then 200 mL of water is added to precipitate the crystalline product; wt 15.00 g; mp 163°–165° C. Recrystallization from methanol gives pure product with the same melting point.

Anal. Calc. for $C_{19}H_{20}N_2O_4$: C, 67.04; N, 5.92; N, 8.23. Found: C, 66.97; H, 5.84; N, 8.24.

EXAMPLE 9

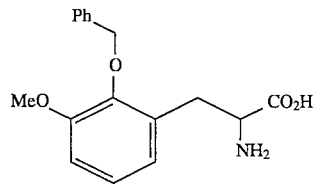

(RS)-3-Methoxy-2-(phenylmethoxy)phenylalanine

A solution (8.50 g, 0.026 mole) of the corresponding hydantoin derivative from Example 6 in 500 mL of 5% sodium hydroxide is heated at reflux for 16 hours. To complete the hydrolysis, the solution is concentrated on the hot plate to ca 150 mL volume over a period of 6 hours. The mixture is cooled and the tacky sodium salt is filtered. The cake is dissolved in 200 mL of water and glacial acetic acid is added to pH 7.2 to precipitate crystals. The crude product is filtered and washed efficiently with cold water; wt 5.90 g. Recrystallization from methanol-ether gives pure racemic amino acid; wt 3.70 g; mp 190°–194° C.

Anal. Calc. for $C_{17}H_{19}NO_4 \cdot 0.1H_2O$: C, 67.35; H, 6.38; N, 4.62; $H_2O$ (KF), 0.59. Found: C, 67.18; H, 6.32; N, 4.53; $H_2O$, 0.80.

EXAMPLE 10

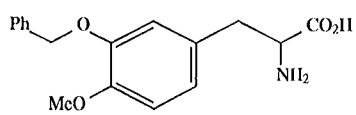

(RS)-4-Methoxy-3-(phenylmethoxy)phenylalanine

This compound is prepared from the corresponding hydantoin derivative (Example 7) by a procedure similar to that in Example 9; tlc (1:5:20 acetic acid-methanol-chloroform system); Rf 0.4 (ninhydrin).

EXAMPLE 11

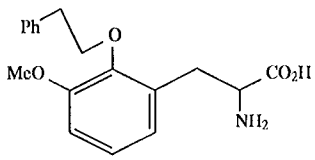

(RS)-3-Methoxy-2-(2-phenylethoxy)phenylalanine

This compound was prepared from the corresponding hydantoin derivative from Example 8 by a procedure similar to that in Example 9; mp 180°–182° C.

Anal. Calc. for $C_{18}H_{21}NO_4$: C, 68.55; H, 6.71; N, 4.44. Found: C, 68.61; H, 6.69; N, 4.46.

EXAMPLE 12

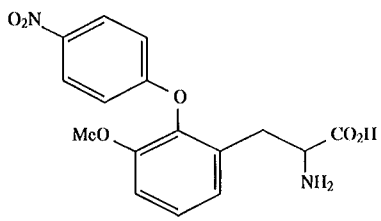

(RS)-3-Methoxy-2-(4-nitrophenoxy)phenylalanine

A mixture of 5.47 g (0.0115 mole) of the malonic ester from Example 41, 150 mL of ethanol, and 100 mL of concentrated hydrochloric acid is heated, with stirring, at reflux overnight. After 20 hours reflux another 50 mL of concentrated hydrochloric acid is added and reflux is continued for 4 hours. The solution is concentrated at reduced pressure and the residue is dissolved in ca 200 mL of water. The turbid solution is clarified (Celite) and concentrated to dryness. The last amounts of water are removed by addition and removal of 3×100 mL of absolute ethanol to give 3.50 g of dry foam. Recrystallization is effected from ethanol-ether to give 2.95 g of pure product as a hydrochloride salt; mp 168°–171° C.

Anal. Calc. for $C_{16}H_{16}N_2O_6 \cdot HCl \cdot 1.25H_2O$: C, 49.11; H, 5.03; N, 7.16; Cl, 9.06. Found: C, 49.26; H, 5.14; N, 7.15; Cl, 8.91.

EXAMPLE 13

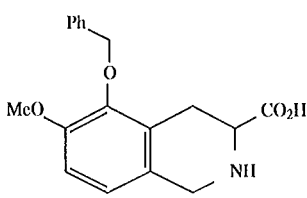

(RS)-1,2,3,4-Tetrahydro-6-methoxy-5-(phenylmethoxy-3-isoquinolinecarboxylic acid A solution of 0.58 g (0.0019 mole) of the phenylalanine derivative from Example 9 in 15 mL of 1N hydrochloric acid is treated with 1.0 mL of methylal and allowed to stand at room temperature overnight. Saturated sodium acetate solution (5 mL) is added to precipitate the free amino acid as a white solid; wt 0.50 g. Recrystallization from methanol gives pure product; mp 236°–238° C. dec.

Anal. Calc. for $C_{18}H_{19}NO_4$: C, 68.99; H, 6.11; N, 4.47. Found: C, 68.64; H, 6.23; N, 4.35.

EXAMPLE 14

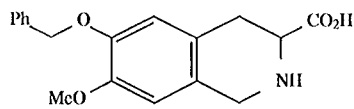

(RS)-1,2,3,4-Tetrahydro-7-methoxy-6-(phenylmethoxy)-3-isoquinolinecarboxylic acid This compound is prepared from the phenylalanine derivative of Example 10 by a procedure similar to that in Example 13; mp 230°–240° C.

Anal. Calc. for $C_{18}H_{19}NO_4$: C, 68.64; H, 6.23; N, 4.47. Found: C, 68.55; H, 6.03; N, 4.41.

EXAMPLE 15

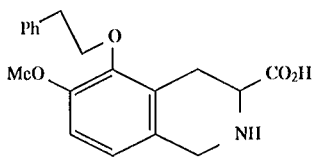

(RS)-1,2,3,4-Tetrahydro-6-methoxy-5-(2-phenylethoxy)-3-isoquinolinecarboxylic acid This compound is prepared from the corresponding phenylalanine derivative of Example 11 by a procedure similar to that in Example 13; mp 232°–235° C.

Anal. Calc. for $C_{19}H_{21}NO_4$: C, 69.70; H, 6.47; N, 4.28. Found: C, 69.33; H, 6.64; N, 4.33.

EXAMPLE 16

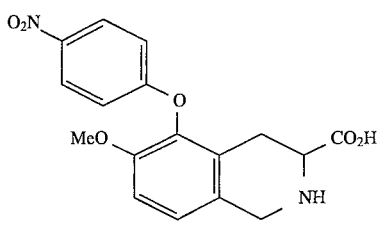

(RS)-1,2,3,4-Tetrahydro-6-methoxy-5-
(4-nitrophenoxy)-3-isoquinolinecarboxylic acid This compound is prepared from the corresponding phenylalanine derivative of Example 12 by a procedure similar to that in Example 13. The product is isolated as a hydrochloride salt from the reaction medium; mp 260°–265° C.

Anal. Calc. for $C_{17}H_{16}N_2O_6 \cdot HCl$: C, 53.76; H, 4.25; N, 7.38. Found: C, 53.29; H, 4.69; N, 7.25.

EXAMPLE 17

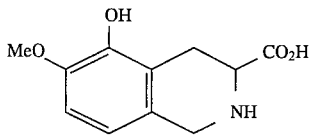

(RS)-1,2,3,4-Tetrahydro-5-hydroxy-6-methoxy-
3-isoquinolinecarboxylic acid

A mixture of 5.01 g (0.016 mole) of the amino acid from Example 13 and 25 mL of concentrated hydrochloric acid is heated at reflux with stirring for 10 minutes. The mixture is cooled and the tacky solid containing benzyl chloride is filtered and washed with 2-propanol and ether; wt 3.80 g (86% yield). Recrystallization from methanol-ether gives pure product, hydrochloride salt; mp 254°–257° C. dec.

Anal. Calc. for $C_{11}H_{13}NO_4 \cdot HCl$: C, 50.87; H, 5.43; N, 5.40. Found: C, 50.69; H, 5.52; N, 5.43.

EXAMPLE 18

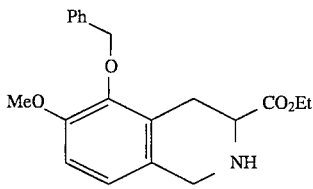

(RS)-1,2,3,4-Tetrahydro-6-methoxy-5-
(phenylmethoxy)-3-isoquinolinecarboxylic acid,
ethyl ester A quantity of 7.85 g (0.025 mole) of the amino acid from Example 13 is dissolved in 1300 mL of warm absolute ethanol (35° C.). Hydrogen chloride gas is passed in until the temperature is 55° C. The solution is allowed to stand at room temperature for 2 days and concentrated to ca 100 mL volume. Ether (200 mL) is added to precipitate the ester as a hydrochloride salt; wt 8.30 g; mp 193°–195° C. Recrystallization from ethanol-ether gives pure hydrochloride salt; mp 193°–195° C.

Anal. Calc. for $C_{20}H_{23}NO_4 \cdot HCl$: C, 63.57; H, 6.40; N, 3.71. Found: C, 63.62; H, 6.49; N, 3.65.

EXAMPLE 19

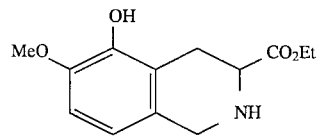

(RS)-1,2,3,4-Tetrahydro-5-hydroxy-6-methoxy-
3-isoquinolinecarboxylic acid, ethyl ester This compound is prepared from the amino acid hydrochloride of Example 17 by a procedure similar to that in Example 18. The product is a hydrochloride salt; mp 213°–214° C. dec.

Anal. Calc. for $C_{13}H_{17}NO_4 \cdot HCl$: C, 54.26; H, 6.30; N, 4.87. Found: C, 54.11; H, 6.27; N, 4.76.

EXAMPLE 20

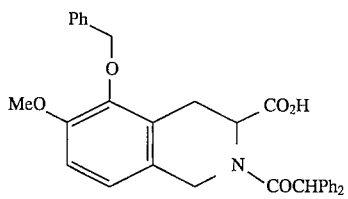

(RS)-2-(Diphenylacetyl)-1,2,3,4-tetrahydro-
6-methoxy-5-(phenylmethoxy)-3-
isoquinolinecarboxylic acid A quantity of 4.55 g (0.01 mole) of 20% tetramethylammonium hydroxide-in-methanol is added to a suspension of 1.56 g (0.005 mole) of the amino acid from Example 13 in 50 mL of methylene chloride. The resulting solution is cooled to 0° C. and, with stirring, a solution of 1.09 g (0.005 mole) of diphenylacetyl chloride in 5 mL of methylene chloride is added. After 5 minutes at 0° C. and one-half hour of warming to room temperature, the methylene chloride is stripped off and water (80 mL) is added. 1N Sodium hydroxide (10 mL) is added to help solution. The supernatant is decanted and the pH is adjusted to pH 2 with 6N HCl to precipitate gum. Ether (10 mL) is added. Crystals develop. The entire mixture is filtered and washed with ether and water; wt 1.40 g. Recrystallization from ethyl acetate-petroleum ether gives 1.20 g (48% yield) of pure product; mp 163°–165° C.

Anal. Calc. for $C_{32}H_{29}NO_5$: C, 75.72; H, 5.76; N, 2.76. Found: C, 75.84; H, 5.72; N, 2.75.

EXAMPLE 21

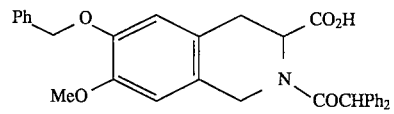

(RS)-2-(Diphenylacetyl)-1,2,3,4-tetrahydro-7-
methoxy-6-(phenylmethoxy)-3-
isoquinolinecarboxylic acid This compound is prepared from the amino acid of Example 14 by a procedure similar to that in Example 20 to give an amorphous solid; mass spectrum (DEI) 507 (M+).

Anal. Calc. for $C_{32}H_{29}NO_5 \cdot 0.7H_2O$: C, 73.88; H, 5.89; N, 2.69. Found: C, 73.89; H, 5.81; N, 2.68.

EXAMPLE 22

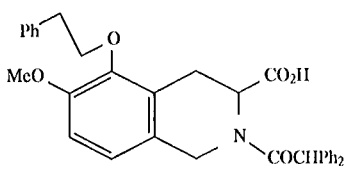

(RS)-2-(Diphenylacetyl)-1,2,3,4-tetrahydro-6-methoxy-
5-(2-phenylethoxy)-3-isoquinolinecarboxylic acid This compound is prepared from the amino acid of Example 15 by a procedure similar to that in Example 20; mp 136°–138° C.

Anal. Calc. for $C_{33}H_{31}NO_5$: C, 75.99; H, 5.99; N, 2.69. Found: C, 75.69; H, 6.03; N, 2.61.

EXAMPLE 23

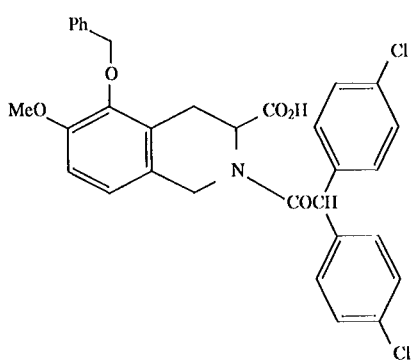

(RS)-2-[Bis(4-chlorophenyl)acetyl]-1,2,3,4-tetrahydro-
6-methoxy-5-(phenylmethoxy)-
3-isoquinolinecarboxylic acid This compound is prepared from the amino acid of Example 13 and bis(4-chlorophenyl)acetyl chloride by a procedure similar to that in Example 20; mp 186°–188° C.

Anal. Calc. for $C_{32}H_{27}Cl_2NO_5$: C, 66.67; H, 4.72; N, 2.42. Found: C, 66.67; H, 4.81; N, 2.42.

EXAMPLE 24

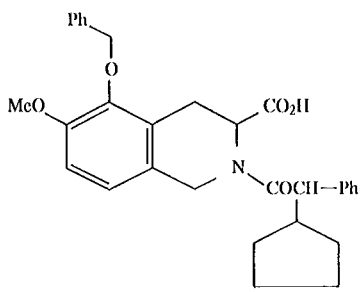

(RS)-2-(Cyclopentylphenylacetyl)-1,2,3,4-tetrahydro-
6-methoxy-5-(phenylmethoxy)-
3-isoquinolinecarboxylic acid This compound is prepared from the amino acid of Example 13 and α-phenylcyclopentaneacetyl chloride by a procedure similar to that in Example 20.

Anal. Calc. for $C_{31}H_{33}NO_5$: C, 74.52; H, 6.61; N, 2.80. Found: C, 73.47; H, 6.82; N, 2.65.

EXAMPLE 25

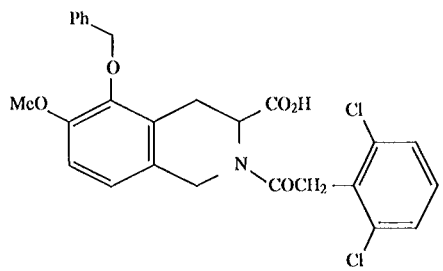

(RS)-2-[(2,6-Dichlorophenyl)acetyl]-1,2,3,4-tetrahydro-
6-methoxy-5-(phenylmethoxy)-
3-isoquinolinecarboxylic acid This compound is prepared from the amino acid of Example 13 and 2,6-dichlorophenylacetyl chloride by a procedure similar to that in Example 20; mp 205°–207° C.

Anal. Calc. for $C_{26}H_{23}Cl_2NO_5$: C, 62.41; H, 4.63; N, 2.80. Found: C, 62.34; H, 4.53; N, 2.81.

EXAMPLE 26

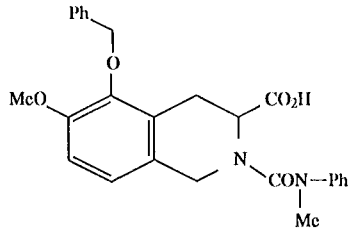

(RS)-1,2,3,4-Tetrahydro-6-methoxy-2-
[(methylphenylamino)carbonyl]-5-
(phenylmethoxy)-3-isoquinolinecarboxylic acid This compound is prepared from the amino acid of Example 13 and N-methyl-N-phenylcarbamoyl chloride by a procedure similar to that in Example 20; mp 134°–136° C.

Anal. Calc. for $C_{26}H_{26}N_2O_5$: C, 69.94; H, 5.87; N, 6.28. Found: C, 69.91; H, 6.00; N, 6.05.

EXAMPLE 27

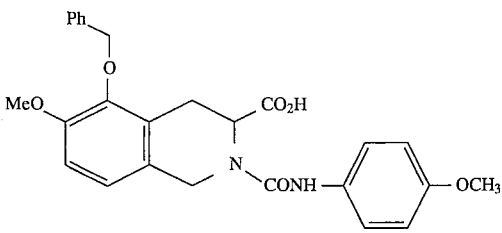

(RS)-1,2,3,4-Tetrahydro-6-methoxy-2-
[[(4-methoxyphenyl)amino]carbonyl]-5-
(phenylmethoxy)-3-isoquinolinecarboxylic acid A solution of 1.49 g (0.01 mole) of p-methoxyphenyl isocyanate in 10 mL of tetrahydrofuran is added dropwise to a stirred mixture of 2.95 g (0.0094 mole) of the amino acid of Example 13, 10.0 mL of 1N sodium hydroxide, and 15 mL of tetrahydrofuran at 10° C. After addition, the reaction mixture is allowed to warm to room temperature over a period of 1 hour. The tetrahydrofuran is stripped off and 150 mL of water and then 3 mL of glacial acetic acid are added to precipitate crude product; wt. 4.00 g. Recrystallization from methanol gives pure product; mp 176°–180° C. dec.

Anal. Calc. for $C_{26}H_{26}N_2O_6$: C, 67.52; H, 5.67; N, 6.06. Found: C, 67.53; H, 5.60; N, 5.86.

EXAMPLE 28

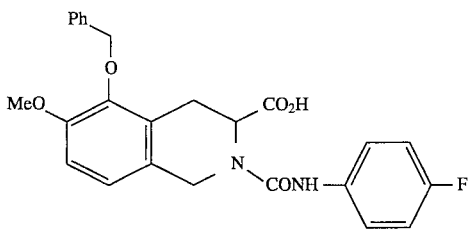

(RS)-2-[[(4-Fluorophenyl)amino]carbonyl
]-1,2,3,4-tetrahydro-6-methoxy-5-
(phenylmethoxy)-3-isoquinolinecarboxylic acid This compound is prepared from the amino acid of Example 13 and 4-fluorophenyl isocyanate by a procedure similar to that in Example 27; mp 186°–187° C. dec.

Anal. Calc. for $C_{25}H_{23}FN_2O_5$: C, 66.66; H, 5.15; N, 6.22. Found: C, 66.43; H, 5.08; N, 6.08.

EXAMPLE 29

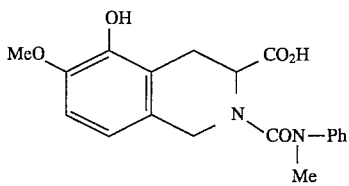

(RS)-1,2,3,4-Tetrahydro-5-hydroxy-6-methoxy-2-
[methyl(phenylamino)carbonyl]-
3-isoquinolinecarboxylic acid At room temperature, a solution of 1.23 g (0.108 mole) of N-methyl-N-phenylcarbamoyl chloride in 5 mL of dioxane is added to a stirred mixture of 2.07 g (0.008 mole) of the compound from Example 17 (hydrochloride salt), 24 mL (0.024 mole) of 1N sodium hydroxide, and 15 mL of dioxane. After 15 minutes at room temperature, the reaction mixture is heated at 75° C. for 5 minutes. The dioxane is removed at reduced pressure. Water (10 mL) and then 16 mL (0.016 mole) of 1N hydrochloric acid is added to precipitate the product; wt 2.00 g (64% yield). Recrystallization from methanol-methylene chloride gives pure crystals; wt 1.50 g; mp 235°–255° C.

Anal. Calc. for $C_{19}H_{20}N_2O_5 \cdot 0.33CH_3OH$: C, 63.27; H, 5.86; N, 7.64. Found: C, 63.27; H, 5.64; N, 7.79.

EXAMPLE 30

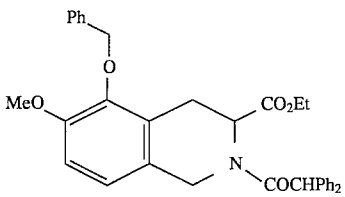

(RS)-2-(Diphenylacetyl)-1,2,3,4-tetrahydro-6-
methoxy-5-phenylmethoxy-
3-isoquinolinecarboxylic acid, ethyl ester A solution of 0.76 g (0.0033 mole) of diphenylacetyl chloride in 5 mL of methylene chloride is added dropwise to a stirred solution of 1.25 g (0.0033 mole) of the compound from Example 18 (hydrochloride), 20 mL of methylene chloride, and 0.74 g (0.0073 mole) of triethylamine. After 15 minutes the solvent is stripped off and 30 mL of ice water and 50 mL of ether are added. The separated ether phase is washed with 25 mL of water, 25 mL of 0.1N hydrochloric acid, and then dried (magnesium sulfate) and concentrated to give 1.20 g of product; mp 111°–113° C. Recrystallization from ethyl acetate-isopropyl ether gives 0.90 g of pure product; mp 114°–115° C.

Anal. Calc. for $C_{34}H_{33}NO_5$: C, 76.24; H, 6.21; N, 2.62. Found: C, 76.23; H, 6.26; N, 2.55.

EXAMPLE 31

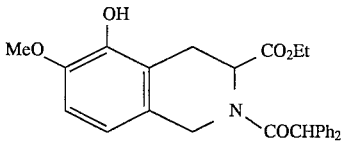

(RS)-2-(Diphenylacetyl)-1,2,3,4-tetrahydro-5-hydroxy-
6-methoxy-3-isoquinolinecarboxylic acid, ethyl
ester This compound is prepared from the amino ester of Example 19 and diphenylacetyl chloride by a procedure similar to that in Example 30; mass spectrum (CI): 446 (M+1).

EXAMPLE 32

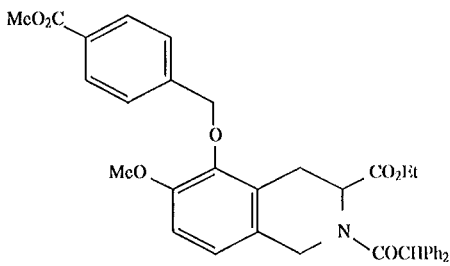

(RS)-5-[(4-Carbomethoxyphenyl)methoxy]-
2-(diphenyacetyl)-1,2,3,4-tetrahydro-6-
methoxy-3-isoquinolinecarboxylic acid, ethyl ester A mixture of 0.89 g (0.002 mole) of the compound from Example 31, 0.69 g (0.003 mole) of 4-carbomethoxybenzyl bromide (Aldrich), 5.0 g of powdered anhydrous sodium carbonate, and 5 mL of DMF is heated at reflux, with stirring, for 5 minutes. The cooled mixture is treated with 50 mL of ice water. The precipitated product is extracted into 150 mL of ether. The solution is dried (magnesium sulfate) and concentrated; wt. of amorphous solid 1.20 g; mass spectrum (CI) 594 (M$^+$).

EXAMPLE 33

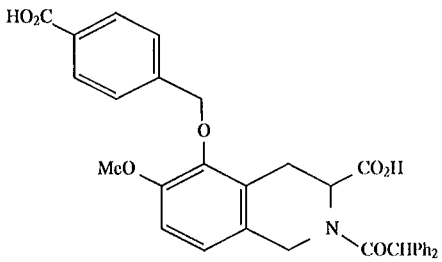

(RS)-5-(4-Carboxyphenylmethoxy)-2-
(diphenylacetyl)-1,2,3,4-tetrahydro-6-methoxy-
3-isoquinolinecarboxylic acid A solution of 1.10 g (0.0019 mole) of the diester from Example 32 in 100 mL of methanol and 15 mL of 2N sodium hydroxide is heated to the boiling point, allowing the methanol to distill off. After 1 hour (pot temperature 90° C.), 1N hydrochloric acid (35 mL) is added to precipitate a gum. On addition of 10 mL of ether, crystals develop; wt. 0.84 g. Recrystallization from ethyl acetate-petroleum ether gives pure product; mp 190°–192° C.

Anal. Calc. for $C_{33}H_{29}NO_7$: C, 71.86; H, 5.30; N, 2.54. Found: C, 71.46; H, 5.15; N, 2.38.

EXAMPLE 34

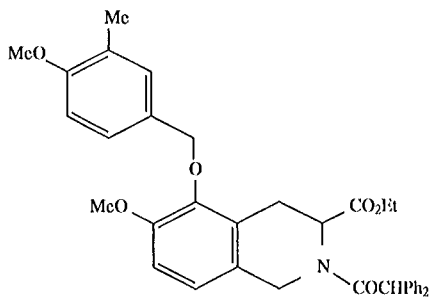

(RS)-2-(Diphenylacetyl)-1,2,3,4-tetrahydro-6-
methoxy-5-[(4-methoxy-3-methylphenyl)
methoxy]-3-isoquinolinecarboxylic acid, ethyl ester This compound is prepared from the phenol derivative of Example 31 and 4-methoxy-3-methyl benzyl chloride by a procedure similar to that in Example 32. The product is purified by silica gel chromatography; tlc (1:1 ethyl-acetate/hexane), one spot, Rf 0.7.

EXAMPLE 35

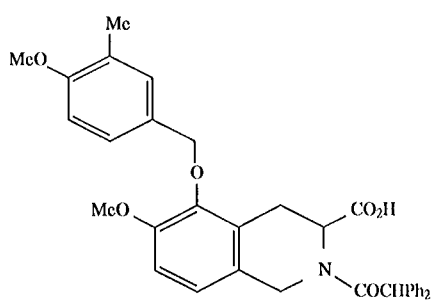

(RS)-2-(Diphenylacetyl)-1,2,3,4-tetrahydro-6-
methoxy-5-[(4-methoxy-3-methylphenyl)
methoxy]-3-isoquinolinecarboxylic acid This compound is prepared by a hydrolysis of the ester from Example 34 as follows: a solution of 0.50 g (0.86 mmole) of the ester, 50 mL of methanol, and 2.0 mL of 1N sodium hydroxide is maintained at reflux for 15 minutes. The methanol is removed, water (30 mL) is added, and 1.0 mL of glacial acetic acid is added to precipitate the gummy product. Purification by silica gel chromatography eluting with 5% methanol-chloroform gives pure product; mp 140°–142° C.

Anal. Calc. for $C_{34}H_{33}NO_6$: C, 74.03; H, 6.03; N, 2.54. Found: C, 73.64; H, 6.04; N, 2.42.

EXAMPLE 36

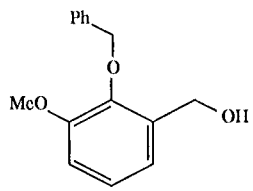

2-Benzyloxy-3-methoxybenzylalcohol

A solution of 43.00 g (0.18 mole) of 2-benzyloxy-3-methoxy-benzaldehyde of Example 1 in 300 mL of absolute ethanol is treated, with stirring, with 7.56 g (0.20 mole) of sodium borohydride. The temperature rises to 50° C. After one-half hour 10 mL of acetone is added, keeping the temperature at less than 60° C. with cooling. After 15 minutes the volatiles are stripped off at reduced pressure. Ice water (500 mL) is added and the product is extracted into 600 mL of ethyl acetate. The dried ($NA_2SO_4$) solution is concentrated. The remaining oil is dissolved in 100 mL of warm ether. Petroleum ether is added to turbidity to give 37.70 g (86% yield) of pure product; mp 58°–60° C.

Anal. Calc. for $C_{15}H_{16}O_3$: C, 73.75; H, 6.60. Found: C, 73.74; H, 6.62.

EXAMPLE 37

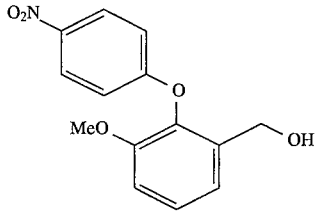

3-Methoxy-2-(4-nitrophenoxy)benzylalcohol

This compound is prepared from the corresponding aldehyde of Example 2 by a procedure similar to that described in Example 36; mp 121°–122° C.; mass spectrum (EI) 275 ($M^+$).

Anal. Calc. for $C_{14}H_{13}NO_5$: C, 61.08; H, 4.76; N, 5.04. Found: C, 60.95; H, 4.73; N, 5.25.

EXAMPLE 38

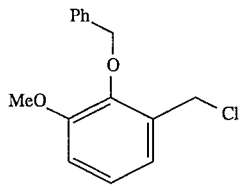

3-(Chloromethyl)-2-phenylmethoxyanisole

A suspension of 92.00 g (0.377 mole) of the alcohol, prepared as in Example 36, in 300 mL of toluene is cooled to 10° C. With stirring, a solution of 75.0 g (0.63 mole) of thionylchloride in 100 mL of toluene is added gradually. Five minutes after addition the reaction is stirred at room temperature for one-half hour. The volatiles are removed at reduced pressure to give 99.0 g (100%) of the product as an oil; tlc (1:1 ethyl acetate-hexane) one spot, Rf 0.8.

EXAMPLE 39

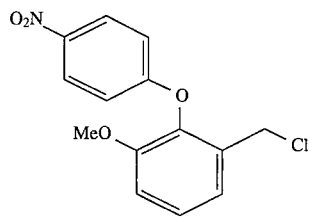

3-(Chloromethyl)-2-(4-nitrophenoxy)anisole

This compound is prepared from the alcohol of Example 37 by a procedure similar to that of Example 38; mp 120°–123° C.; mass spectrum (EI) 293 ($M^+$).

EXAMPLE 40

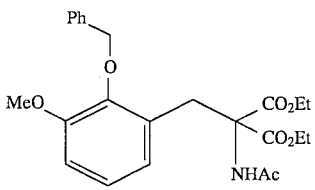

2-(Acetylamino)-2-[[3-methoxy-2-(phenylmethoxy)phenyl]methyl]-propanedioic acid, diethyl ester A quantity of 136.20 g (0.42 mole) of 21 wt. % sodium ethoxide-in-ethanol is added to a stirred solution of 90.14 g (0.415 mole) of diethyl acetamidomalonate (Aldrich) in 800 mL of absolute ethanol. A solution of the benzyl chloride derivative of Example 38 in 500 mL of absolute ethanol is added and the mixture is heated at reflux for 2 hours. The cooled mixture is poured into 4 L of ice and water containing 20.0 g of glacial acetic acid. The supernatant is decanted from the separated gum. The gum is dissolved in 2 L of ether, the solution dried (magnesium sulfate), and concentrated to ca 300 mL volume. Petroleum ether (100 mL) is added to precipitate 107.1 g (66.4% yield) of pure crystalline product; mp 94°–96° C.

Anal. Calc. for $C_{24}H_{29}NO_7$: C, 65.00; H, 6.59; N, 3.16. Found: C, 65.12; H, 6.75; N, 3.13.

EXAMPLE 41

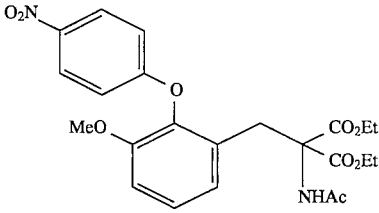

(Acetylamino)[[3-methoxy-2-(4-nitrophenoxy)phenyl]methyl]-propanedioic acid, diethyl ester A quantity of 0.50 g (12.5 mole) of 60% sodium hydride oil is rinsed with dry tetrahydrofuran (5 mL). The THF is decanted and 20 mL of DMSO is added to the NaH under nitrogen. With stirring 2.50 g (11.5 mole) of diethyl acetamidomalonate is added to give vigorous evolution of hydrogen. After 2 hours at room temperature, 3.00 g (10.2 mole) of the benzyl chloride of Example 39 and 0.30 g (2.0 mole) of sodium iodide (pulverized) are added. The mixture is stirred for 3 days and poured into ca 300 mL of ice water containing 2 mL of glacial acetic acid. The resulting precipitate is extracted into ethyl acetate. The extract is washed with water and 5% sodium thiosulfate solution, dried (magnesium sulfate), and concentrated to give 4.64 g (96%) of crude product. Recrystallization from ethyl acetate gives pure product; mp 189°–190° C.; mass spectrum (DEI) 474 (M+).

Anal. Calc. for $C_{23}H_{26}N_2O_9$: C, 58.22; H, 5.52; N, 5.90. Found: C, 58.39; H, 5.54; N, 5.99.

EXAMPLE 42

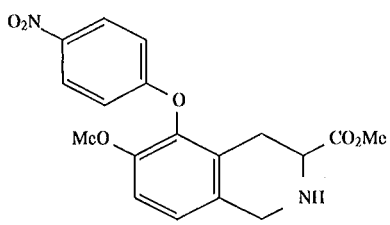

(RS)-1,2,3,4-Tetrahydro-6-methoxy-5-(4-nitrophenoxy)-3-isoquinolinecarboxylic acid, methyl ester A solution of 1.00 g (0.0026 mole) of the amino acid (hydrochloride salt) of Example 16 in 75 mL of methanol is saturated with hydrogen chloride gas, allowing the temperature to rise to near the boiling point. The solution is allowed to stand at room temperature overnight. The separated white crystals are filtered and washed with 50% methanol-ether to give 0.86 g of pure amino ester product as a hydrochloride salt; mp 237°–239° C. dec.

Anal. Calc. for $C_{18}H_{18}N_2O_6 \cdot HCl$: C, 54.76; H, 4.85; N, 7.10. Found: C, 54.51; H, 4.81; N, 7.00.

EXAMPLE 43

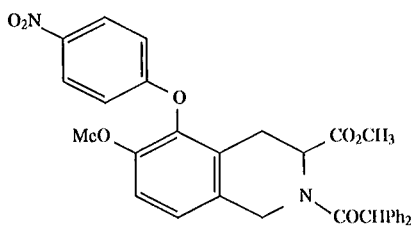

(RS)-2-(Diphenylacetyl)-1,2,3,4-tetrahydro-6-methoxy-5-(4-nitrophenoxy)-3-isoquinolinecarboxylic acid, methyl ester A solution of 0.35 g (1.30 mole) of diphenylacetyl chloride in 2 mL of acetonitrile is added to a stirred mixture of 0.60 g (1.50 mole) of the amino ester hydrochloride of Example 42, 8 mL of acetonitrile, and 0.33 g (3.30 mole) of triethylamine. After 1 hour the mixture is poured into 50 mL cold 2% potassium bisulfate solution. The supernatant is decanted from the gum. The gum is extracted into 50 mL methylene chloride. The solution is dried (magnesium sulfate), charcoaled, filtered, and concentrated to give 0.81 g of pure product as a solid foam.

Anal. Calc. for $C_{32}H_{28}N_2O_7$: C, 69.56; H, 5.11; N, 5.07. Found: C, 69.29; H, 5.19; N, 4.78.

EXAMPLE 44

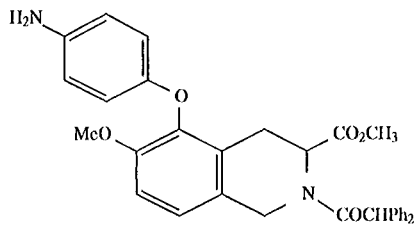

(RS)-5-(4-Aminophenoxy)-2-(diphenylacetyl)-1,2,3,4-tetrahydro-6-methoxy-3-isoquinolinecarboxylic acid, methyl ester A solution of 0.80 g (1.45 mole) of the nitrobenzene derivative of Example 43 in 50% methanol-THF is reduced with 5% palladium-on-carbon catalyst. The filtered solution is concentrated at reduced pressure to give 0.75 g of pure product as a solid foam; mass spectrum (EI) 522 (M+).

Anal. Calc. for $C_{32}H_{30}N_2O_5$: C, 73.55; H, 5.79; N, 5.36. Found: C, 72.37; H, 5.76; N, 5.06.

EXAMPLE 45

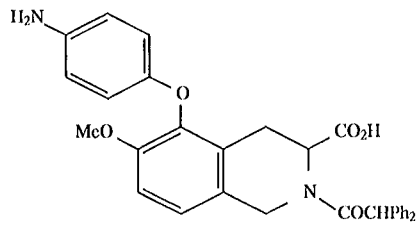

(RS)-5-(4-Aminophenoxy)-2-(diphenylacetyl)-1,2,3,4-tetrahydro-6-methoxy-3-isoquinolinecarboxylic acid This compound is prepared by hydrolysis of the corresponding ester of Example 44 by a procedure similar to that of Example 35; mass spectrum (FAB) 509.2 (M+1).

EXAMPLE 46

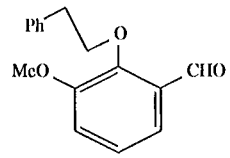

3-Methoxy-2-(2-phenylethoxy)benzaldehyde

A mixture of 111.0 g (0.73 mole) of o-vanillin, 130 g (0.70 mole) of β-phenethyl bromide, 1 L of DMF, and 300 g of anhydrous powdered potassium carbonate is heated with stirring at reflux for 3 hours. The cooled mixture is added to 2 L of ice water. The separated product is extracted with 1 L of ether. The ether solution is washed with 500 mL of 1N sodium hydroxide, dried (potassium carbonate), and concentrated to ca 300 mL volume. Hexane is added to turbidity and this solution is passed through a column of silica gel, eluting first with hexane to remove fast spot (Rf 0.9, 1:1 hexane-ethyl acetate, tlc system) and then with ethyl acetate to obtain 87.1 g (49%) of product; tlc (1:1 hexane-ethyl acetate) Rf 0.8.

EXAMPLE 47

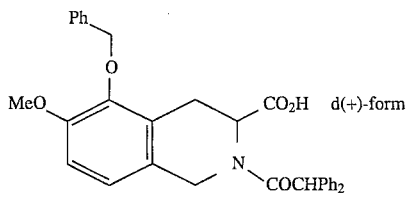

(+)-2-(Diphenylacetyl)-1,2,3,4-tetrahydro-6-methoxy-5-(phenylmethoxy)-3-isoquinolinecarboxylic acid A quantity of 0.342 g (0.67 mole) of the compound from Example 20 is dissolved in 10 mL of ethyl acetate. The solution is treated with 0.083 g (0.67 mole) of 98% 1 (−)-α-methylbenzylamine. Petroleum ether is added until slightly turbid. Crystals separate on inducement; wt 0.185 g; mp 147°–149° C. Recrystallization from ethyl acetatepetroleum ether give the purified, least soluble diastereomeric salt; mp 157°–159° C. Regeneration of the free acid is accomplished by dissolution of the salt in a minimum amount of methanol and precipitation of the amorphous product (mp 80°–91° C.) with excess 1% potassium bisulfate solution; $[\alpha]_D^{23}$+17.44° (0.9% MeOH).

Anal. Calc. for $C_{32}H_{29}NO_5 \cdot 0.3H_2O$: C, 74.92; H, 5.82; N, 2.73. Found: C, 74.54; H, 5.42; N, 2.49.

EXAMPLE 48

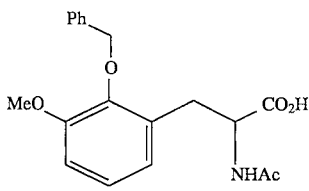

(RS)-N-Acetyl-3-methoxy-2-(phenylmethoxy)phenylalanine

A quantity of 300 mL of 1N sodium hydroxide is added to a hot solution of 44.40 g (0.10 mole) of the compound of Example 40 in 500 mL of methanol. The resulting mixture is heated on the steam bath, allowing the methanol to distill over (1 hour). Water (500 mL) is added and the supernatant is decanted from some gum. 6N Hydrochloric acid is added to the decantate to pH 3. $CO_2$ is vigorously liberated as crude solid separates.

Recrystallization from methanol-water gives 21.3 g (62% yield) of product; mp 169°–170° C.

Anal. Calc. for $C_{19}H_{21}NO_5$: C, 66.46; H, 6.17; N, 4.08. Found: C, 66.37; H, 6.39; N, 4.02.

We claim:

1. A method for treating disorders associated with excessive AVP secretions in a mammal suffering therefrom which comprises administering a therapeutically effective amount of a compound of Formula I

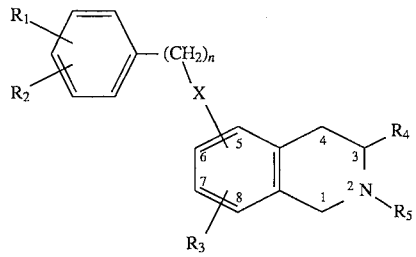

or a pharmaceutically acceptable salt thereof wherein:

$R_1$ and $R_2$ are each independently hydrogen, lower alkyl, halogen, hydroxy, alkoxy, amino, alkylamino, dialkylamino, acylamino, $CF_3$, carboxy, carboalkoxy, hydroxyalkyl, aminoalkyl, and nitro;

n is an integer from zero to 4;

x is absent, O, S, NH, N-alkyl, and is attached to the tetrahydroisoquinoline at the 5 or 6 position;

$R_3$ is hydrogen, alkoxy, aralkoxy, alkylthio, or halogen;

$R_4$ is hydrogen, alkyl, hydroxyalkyl, $CO_2R_6$, $CON(R_6)_2$ wherein $R_6$ is hydrogen or lower alkyl; and $R_5$ is alkyl, aryl, aralkyl which can be unsubstituted or substituted on the alkyl and/or on the aryl portion, diaralkyl the aryl portion can be unsubstituted or substituted, $COR_7$, $SO_2R_7$ wherein $R_7$ is aralkyl, alkyl, diaralkyl, $OR_8$, $NR_8R_9$ wherein $R_8$ and $R_9$ are each independently hydrogen, alkyl, cycloalkyl, aryl, or aralkyl wherein aryl is phenyl or naphthyl and the substituents are one or more selected from: alkyl, alkoxy, hydroxy, halogen, $NO_2$, $NH_2$, NHalkyl, $N(alkyl)_2$, SCH, and SH together with a pharmaceutically acceptable carrier.

* * * * *